United States Patent [19]

Winefordner et al.

[11] Patent Number: 5,088,820

[45] Date of Patent: Feb. 18, 1992

[54] LASER ENHANCED IONIZATION DETECTOR FOR RAMAN SPECTROSCOPY

[75] Inventors: James D. Winefordner; Benjamin W. Smith, both of Gainesville, Fla.

[73] Assignee: University of Florida, Gainesville, Fla.

[21] Appl. No.: 578,839

[22] Filed: Sep. 7, 1990

[51] Int. Cl.$^5$ ............................................... G01J 3/44
[52] U.S. Cl. ................................................... 356/301
[58] Field of Search ........................................ 356/301

[56] References Cited

PUBLICATIONS

Esherick et al, "Ionization Detected Raman Studies of the 1600 cm$^{-1}$ Fermi Dyad of Benzene", J. Chem. Phys., 10/1/85, vol. 83, #7, pp. 3311-3317.

*Primary Examiner*—F. L. Evans
*Assistant Examiner*—K. P. Hantis
*Attorney, Agent, or Firm*—Kerkam, Stowell, Kondracki & Clarke

[57] ABSTRACT

Raman spectroscopy uses a resonance ionization detector. In particular, a first laser source is provided for application of laser energy to a sample cell. A second laser source provides energy to the ionization detector, which ionization detector includes metal vapor having at least three energy states or levels. The laser from the second laser source has a frequency such that it will promote the metal vapor from one of its levels to a higher level, whereas the first laser source is tunable such that upon Raman scatter from the sample cell promoting the metal vapor as well, the metal atoms will be ionized and the ionization detector will detect the scatter from the sample material. The scatter from the sample cell is provided to the ionization detector by way of an optical coupler such as a lens. The ionization detector may be a flame-type ionization detector, a metal vapor cell ionization detector, for a glow discharge tube (such as a hollow cathode lamp) ionization detector.

17 Claims, 2 Drawing Sheets

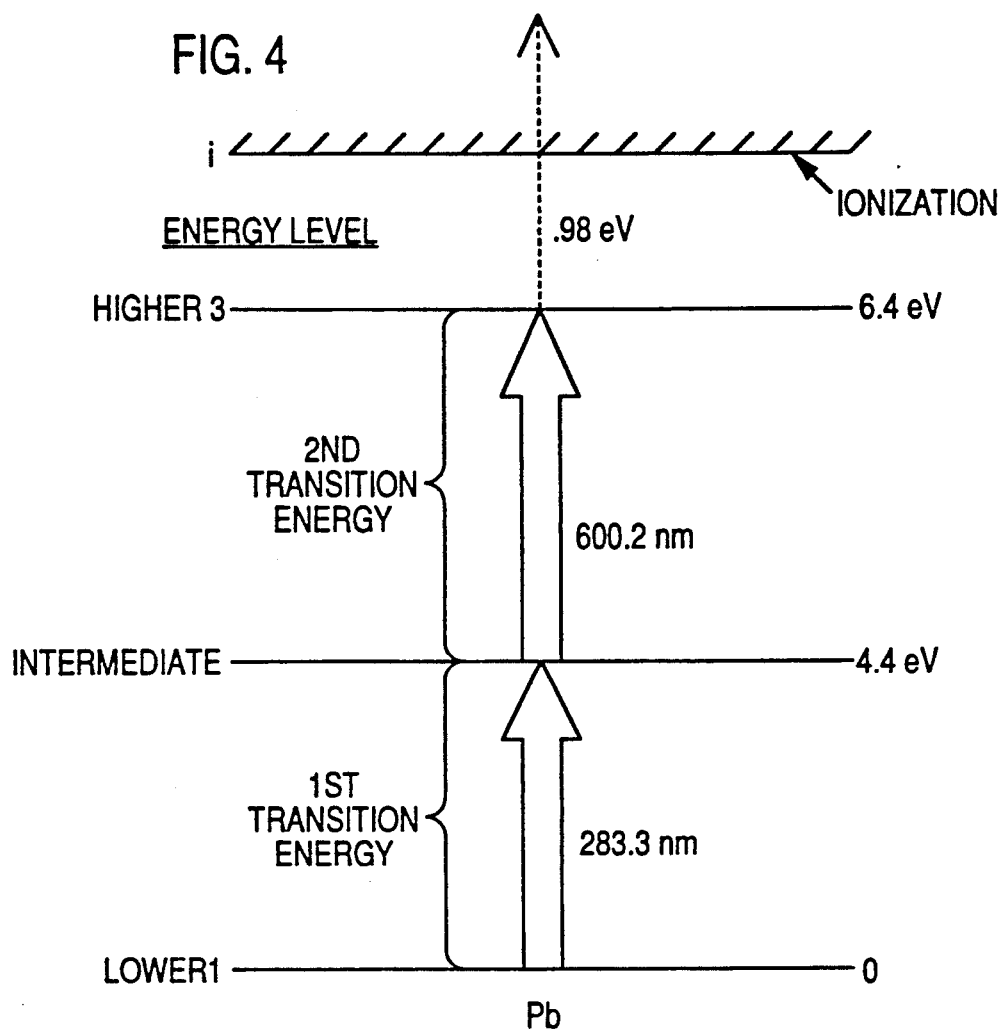
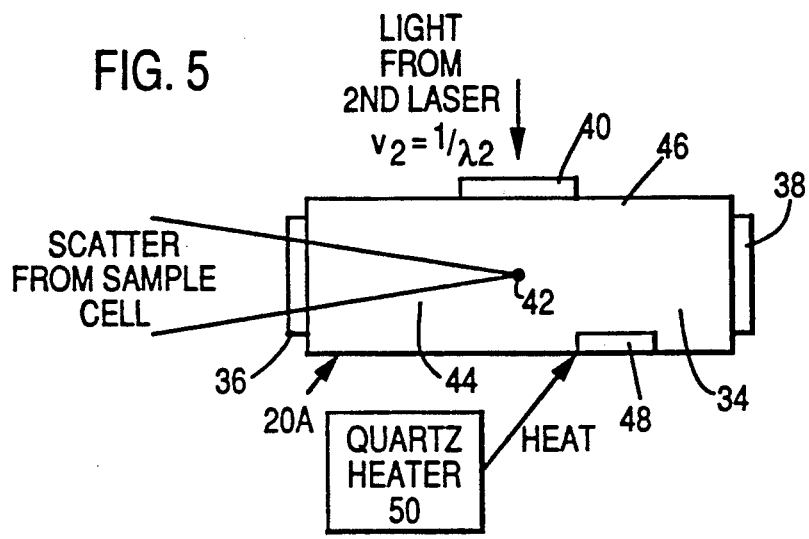

LASER ENHANCED IONIZATION DETECTOR FOR RAMAN SPECTROSCOPY

BACKGROUND OF THE INVENTION

This invention relates to Raman spectroscopy. More specifically, this invention relates to use of a laser enhanced ionization detector connection with Raman spectroscopy.

The detection of one spectroscopic process by observing its affect upon another spectroscopic process is termed resonance detection. Such detectors have been resonance monochromators, especially used to detect atomic fluorescence. The use of resonance monochromators for atomic fluorescence has been based primarily upon the generation and detection of fluorescence in a separate cell. However, Matveev has proposed in the Journal of Analytic Chemistry U.S.S.R., 38,561 (1983) an ionization detector for laser excited atomic fluorescence.

Raman spectroscopy involves the application of an intense beam of monochromatic radiant energy to a sample gas, liquid, or solid. Under these circumstances, a small fraction of the energy is scattered. In addition to the original frequency of the applied radiation, the scattered radiation contains a small fraction at a lower frequency and an even smaller fraction of radiation at a higher frequency. The differences between the frequencies of applied radiation and the scattered rays correspond to vibration and rotation frequencies of the irradiated molecules. Thus, Raman spectroscopy may be used to reveal the fundamental frequencies of molecules from measurements. The measurements are usually in the visible and ultraviolet part of the electromagnetic spectrum and Raman spectroscopy often supplements infrared spectroscopy.

A known approach to Raman spectroscopy involves inducing the Raman scatter by a laser, collecting the scatter by suitable optics, transferring the Raman scatter to a double or triple monochromator, and detecting by use of a photomultiplier tube. Spectra are obtained by scanning the monochromator over a wavelength region near to the wavelength of the laser which is producing the Raman scatter. Although Raman spectroscopy has been quite useful, there are problems in its application. In particular, the intensity of scattered light and the efficiency of detection are very low. Accordingly, the sensitivity of the technique is poor, usually limited to concentrations of 0.1% and greater. In addition, spectra may not be obtained, except with great difficulty, at wavelengths close to the exciting laser because of stray light produced in the monochromator by Rayleigh scattering from the sample. The Rayleigh scatter from a fixed wavelength excitation laser makes it necessary to use a large double spectrometer with poor optical efficiency.

A more recent approach to Raman spectroscopy involves laser induced scatter occurring in the near infrared region. The scatter is collected and transferred by suitable optics (including a source line rejection filter) to a Michelson interferometer and detected by a photodiode. The produced interferogram is treated by Fourier transformation to give the Raman spectrum. Although this approach is useful to a certain extent, the rejection of stray laser light scatter again causes a loss of signal (and thus lowers signal-to-noise ratio). This results in poor detection limits even when resonance enhancement and/or surface enhancement techniques are used. The conventional and interferometer approaches also are characterized by restricted spectral ranges which are limited at the low energy end by the laser profile, laser intensity, and spectral rejection of the system, and by a nominal resolution which is often limited by the need for reasonable spectral band pass in the dispersive system or short mirror near travel in the interferometer.

A spectroscopic scheme for lithium is shown in FIG. 1 and will be used to explain the operation of a known laser enhanced ionization device of FIG. 2. Two strong bound-bound transitions are used, one, at 670.78 nm originating from the ground state and terminating at a level of 14904 cm$^{-1}$ and the other, at 460.29 nm beginning at that level and terminating at 36623 cm$^{-1}$, 0.85 eV below the ionization limit. If two optically saturating laser beams enter coincidentally into a lithium atomic vapor (eg., an air/$H_2$ flame into which a lithium solution has been introduced) at these wavelengths, the promotion of lithium to the ionic state can be made to be 100% efficient due to the efficiency with which excited species in the 36623 cm$^{-1}$ level are collisionally ionized. Moreover, the collection of these charged species can be 100% efficient within the electric field provided by the immersed electrode. Such an experiment is the basis for the technique of Laser Enhanced Ionization (LEI) which has been used successfully for the sensitive detection of many atomic species.

With reference now to FIG. 2, the electrode is supplied with a negative high voltage and the base of the burner serves as the other electrode. Lasers of two frequencies enter the space between the burner and the electrode. One of the frequencies corresponds to the transition from the ground state to the first excited state in FIG. 1 whereas the other of the laser wavelengths corresponds to the transition from the first excited state to the second or higher excited state. The flame from the burner is used to provide the energy needed to ionize the sample gas which is supplied to the burner.

The device of FIG. 2 is a true resonance device in that the spectroscopic transition being detected is the same as the transition within the resonance monochromator. The device or system of FIG. 2 is useful for detecting atomic species, but is not applicable to the detection of Raman scatter.

OBJECTS AND SUMMARY OF THE INVENTION

Accordingly, it is a primary object of the present invention to provide new and improved Raman detection.

A more specific object of the present invention is to provide an apparatus and method for Raman detection which has greatly improved sensitivity and relatively high signal-to-noise ratio.

Further objects of the present invention is to avoid or minimize the previous problems noted with respect to Raman detection.

The above and other objects of the present invention which will become more apparent as the description proceeds are realized by an apparatus for Raman spectroscopy including a sample cell for holding sample material upon which Raman analysis is to be performed. A first laser source is tunable for applying laser energy having a variable wave number to sample material within the sample cell. A resonance ionization detector ("RID") has a metal vapor which exists at lower, intermediate, and higher energy levels, the higher energy level being at or near ionization. A difference between the lower and intermediate energy levels corresponds to a first transition energy, whereas a difference between the intermediate and higher energy levels corresponds to a second transition energy. A second laser source applies energy having a known wave number to the metal vapor of the ionization detector, the known wave number corresponding to the second transition energy. An optical coupler transfers Raman scatter from the sample cell to the RID such that, upon the first laser source being tuned to produce Raman scatter at a wave number corresponding to the first transition energy and laser excitation of the RID at the second transition energy, ionization is detected by the resonance ionization detector. The resonance ionization detector is preferably selected from the following burner ionization detector, a metal vapor cell ionization detector, and a glow discharge tube ionization detector. The metal vapor preferably comprise a metal selected from the group consisting of I A, II B, III A, or IV A elements. The most preferred metal vapors are lithium or lead. Preferably, the known wave number corresponds to the second transition energy and the first transition energy is provided by the Raman scatter as discussed above, but the known wave number could alternately correspond to the first transition energy and the second transition energy could be provided by Raman scatter.

The present invention may alternately be described as a method for Raman spectroscopy comprising the steps of placing sample material for Raman analysis in a sample cell; applying laser energy of a variable wave number to the sample material within the sample cell; generating a metal vapor within a resonance ionization detector, the metal vapor existing at lower, intermediate, and higher energy levels, the upper energy level being at or near ionization. A difference between the lower and intermediate energy levels corresponding to a first transition energy, a difference between the intermediate and the higher energy levels corresponding to a second transition energy. Laser energy is applied to the metal vapor in the RID at a known wave number corresponding to the second transition energy. Raman scatter is transferred from the sample cell to the resonance ionization detector such that, upon the laser energy of variable wave number which is applied to the sample material being tuned to produce Raman scatter at a wave number corresponding to the first transition energy, ionization is detected by the RID. The method further includes the step of generating a Raman spectra of the sample material.

BRIEF DESCRIPTION OF THE DRAWINGS

The above and other features of the present invention will be more readily understood when the following detailed description is considered in conjunction with the accompanying drawings wherein like characters represent like parts throughout the several views and in which:

FIG. 4 is a transition chart for lead; and

FIG. 5 is a metal vapor cell ionization detector according to the present invention.

DETAILED DESCRIPTION

In the discussion which follows, reference will be made to the wave number of electromagnetic energy. As is well known, the wave number is the reciprocal of the wavelength and is commonly referred to by use of the Greek mu. However, the description which follows will use the lower case v in order to refer to a wave number of a particular laser or light energy.

Figure 3:
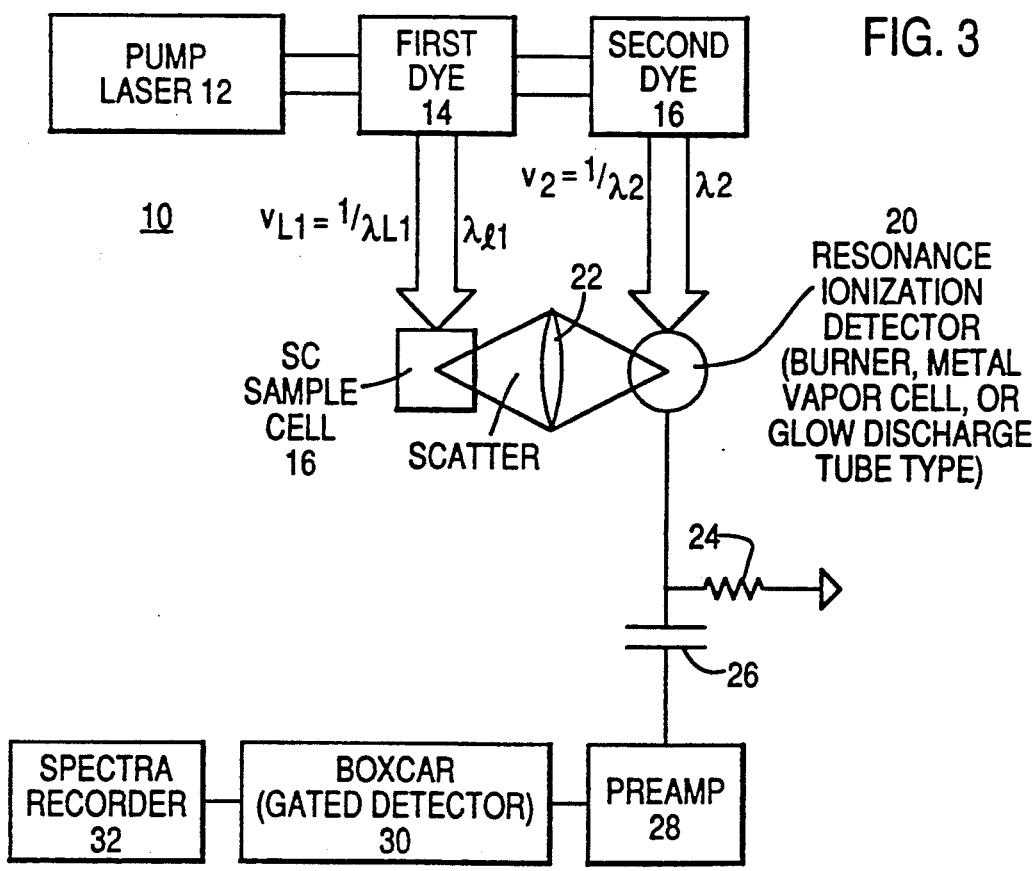
FIG. 3 is a schematic illustrating the present invention.

With reference now to FIG. 3, the apparatus 10 according to the present invention will be discussed. A pump laser 12 is used to generate two different laser lights or sources. In particular, the pump laser 12 supplies energy to a first dye laser 14. The first dye laser 14 portion or laser source then supplies light to a sample cell 16 in which sample material (not separately shown) has been disposed. The sample material may be a gas, liquid, or solid from which one wants to determine the Raman spectra. The first dye 14 provides for a tunable laser source so that the wave number $v_{L1}$ is variable.

The pump laser 12 is also connected to a second dye 18 in order to provide a second laser source generating laser light at a fixed wave number $v_2$. Various known types of laser arrangements could be used. More specifically, the dye lasers could be cw (continuous wave: $Ar^+$ or $Kr^+$ or Nd-YAG pumped) or pulsed (Excimer, Nd-YAG, or Cu-vapor pumped).

Light from the second dye laser source 18 is provided to a resonance ionization detector (RID) 20. In addition to receiving the light at a known fixed wave number $v_2$, the RID 20 receives scatter from the sample cell 16 by way of an optical coupler. Although various optical coupling arrangements could be used, the illustrated optical coupler is a lens 22.

The RID 20 may work using modifications of known ionization detection schemes or using new ionization detection schemes. The RID 20 may include an electrode or electrodes (not separately shown in FIG. 3 but shown and discussed in detail below) which supply a signal to a filter having resistor 24 and capacitor 26 and on to a preamplifier 28. The preamplifier 28 may supply a boxcar 30 which is a known type of gated detector. The boxcar 30 in turn is connected to a recorder 32. The recorder 32 simply records the ionization detected by the RID 20 dependent upon the wave number $v_{L1}$. The operation of the components 24, 26, 28, 30, and 32 are well known and relatively standard, they need not be discussed in further detail.

Figure 1:
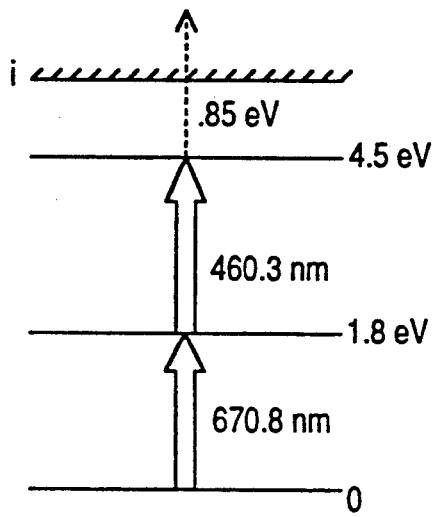
FIG. 1 illustrates a spectroscopic scheme for lithium.
Figure 2:
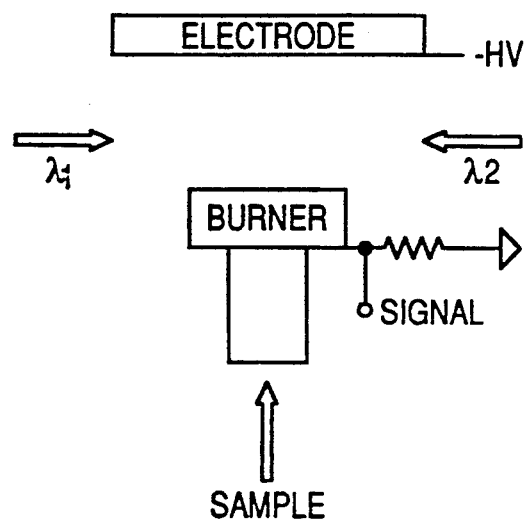
FIG. 2 illustrates a prior art laser enhanced ionization technique.

The RID 20 may operate as a flame-type RID. In that case, the RID operates with a principle of operation somewhat similar to that of FIG. 2. In particular, such a flame-type RID would use the second dye laser source 18 to provide the energy for transition of lithium from its intermediate state to its higher state, whereas the scatter from the sample cell would be provided to the lithium or other metal in the RID to elevate the lithium from its ground or lower state to the intermediate state. In other words, a flame RID would have the same transitional arrangement as FIG. 1 assuming that lithium was used. Other materials could be used as will be discussed in detail below. However, unlike the arrangement of FIG. 2, two laser beams are not directed against the material within the flame. Instead, this variation would have a single laser beam directed towards the flame, whereas the second beam of energy corresponds to the Raman scatter from a separate sample cell. Additionally, the RID according to this arrangement is different from FIG. 2 in that a sample is not being provided to the flame for analysis purposes. Instead, the chamber in which the flame occurs is provided with a source of atoms, such as lithium atoms. The lithium atoms are not the material which is being analyzed, but are used to provide the transitional states like that of FIG. 1. Simple RID cell could be an atmospheric pressure $H_2$-air flame containing lithium (nebulization of 100 micrograms/milliliters at approximately 1 milliliter/minute). In the variation of FIG. 2 which could be used as an RID, the electrode and the burner should be out of the path of the light beams in order to avoid undesirable sources of inaccuracy.

As an alternative to the flame RID, a low pressure metal vapor cell RID might be used. With reference now to FIG. 5, such an arrangement is shown. FIG. 5 shows such a metal vapor cell as 20A and includes a housing 34 which is preferably made of quartz. The housing 34 includes a first window 36 to allow entry of scatter from the sample cell and a second window 38 to allow the scatter to pass out of the housing 34. A third window 40 allows light from the second laser (second dye 18 of FIG. 3) to pass into the housing 34. The light from the sample cell or the scatter if focused at point 42 centrally located within the housing 34. Electrodes 44 and 46 are used to detect the ionization in known fashion. A charge would be placed across the electrodes 44 and 46 and the current would be detected in order to detect ionization. The electrodes 44 and 46 are shown as dots in FIG. 5 as they would be wires extending normal to the plane of view of FIG. 5. The electrodes 44 and 46 should be disposed out of the path of the scatter from the sample cell and the light from the second laser to avoid introducing inaccuracies. Within the housing 34 is a lithium source 48, although other metals could be used to supply the metal vapor. A quartz heater 50 is shown schematically and is used to heat the metal source 48 to provide a metal vapor within the chamber of housing 34 when ionization is to be detected. The RID of FIG. 5 is somewhat different from the flame ionization detector discussed above in that the quartz heater is used to provide the atoms of metal vapor and the scatter promotes the metal atoms from a lower energy state to an intermediate energy state and the light from the second laser source promotes the atoms from the intermediate energy level to a higher energy level which is at the ionization state. In other words, there is no flame to boost the energy of the atom to the ionization state, but this may be done directly by the laser energy. The housing 34 could be made of quartz and placed in a furnace for heating purposes.

The flame type ionization detector could be structured in somewhat similar fashion to the arrangement of FIG. 5 except that the electrodes 44 and 46 would be replaced by a single electrode combined with a burner base serving as the second electrode and both the electrode and burner base would be disposed out of the light from the scatter and the second laser. Additionally, a source of metal vapor would be provided to the flame-type ionization detector.

A third type of ionization detector which might be used would be a glow discharge tube such as a hollow cathode lamp. The cathode lamp type ionization detector in that it allows one to provide atoms for the metal vapor by way of sputtering. This may allow one to use different materials, other than those which are most useful for the flame-type and the metal vapor cell ionization detectors.

It should be noted that, in the case of pulsed lasers, there should be proper temporal and spatial overlap of the Raman pulse and the pulse of the second laser within the RID. In other words, one must simply time the pulses so that the scatter from the sample cell reaches the RID at the same time as the pulse from the second laser and the light energy from both of these sources is provided at the same location or zone within the RID.

An alternative to lithium, various other metal which provide a high vapor pressure at relatively low temperatures could be used. Metals from group I A (such as lithium discussed above), II B (such as zinc), III A (such as thallium), and IV A (such as lead) could be used. The transitional scheme for lead is shown in FIG. 4, but FIG. 4 more generally shows the scheme for various other materials on the left side. That is, a first transition energy promotes the atom from a lower energy level to an intermediate energy level, whereas a second transition energy promotes the atom from the intermediate excited state to a higher excited state which is at or near the ionization level. The right side of FIG. 4 shows particular wavelengths corresponding to lead, but the general concept for other materials will be readily appreciated. It should also be noted that the specific materials identified above are not the only materials which could be used by the present invention. More specifically, and as mentioned above, use of a hollow cathode lamp or other type of glow discharge tube may allow one to provide atoms by sputtering and use many different materials.

The Raman-RID system as described should be immune to scatter emission, and fluorescence, except that which spectral overlaps the absorption line profile of the metal used in the RID. In addition the Raman RID should allow a much larger radiation throughput than conventional Raman systems and therefore much larger Raman signals. Since the RID should have extremely low noise levels, the Raman limits of detection are excellent. Finally, because of the narrow dye laser lines and the narrow absorption half-width of the Doppler broadening line of the metal in the hollow cathode and glow discharge RIDs, the system should be capable of measuring Raman spectra over a range starting from less than 100 cm$^{-1}$ (depending upon the absorption profile of the metal in the RID) to an upper limit depending on the dye used in the first laser.

The main source of sample cell background in the case of Raman spectroscopy of molecules in the condensed phase is background fluorescence from concomitants and possibly the analyte itself. Of course, as long as the first laser wavelength is sufficiently long (much greater than 650 nm), fluorescence should be minimal or non-existent. In the case of resonance Raman spectroscopy, fluorescence is possible from the analyte or interferents.

In the gas phase, additional noise sources may arise from thermal emission, such as combustion flames or plasmas, and coincidental line emission at the wave number corresponding to the first transitional energy. However, both of these noise sources should seldom produce RID shot noise currents approaching the inherent shot noise in the background current of the RID.

Any process in the sample cell, including Raman scatter, fluorescence, and thermal emission increases the average background current in the RID will increase the electron number shot noise.

Although the above factors may supply some noise to the system, the system will still provide high signal-to-noise ratios, great sensitivity, and a high level of accuracy. It should also be noted that the signal-to-noise ratio of a pulsed Raman-RID is believed to be superior to that of the cw Raman-RID. With respect to the materials mentioned above, the lithium is suitable for spontaneous Raman (SR) operation and surface enhanced spontaneous Raman (SER), whereas the lead is suitable for resonance Raman (RR) or surface enhanced resonance Raman (SERR).

As mentioned previously, the sample cell can be either a solution, a solid, or a gas. In the case of a gas, the gas may be a non-emitting gas, a combustion flame, or even a plasma. The high spectral selectivity and freedom from scatter interference should allow measurements even within a luminous background media. To scan a Raman spectrum, the second dye laser is set at the second transition energy and the first dye laser is scanned while recording the ionization signal. The spectral range at the low wave number end and the spectral resolution will be determined by the convolution of the Raman scatter spectral profile due to natural Raman broadening processes, the first laser spectral profile, and by the absorption half-width and profile of the metal in the RID. The spectral range at the high end will be determined by the dye used in the first dye laser. As should be noted, the signal-to-noise ratio will increase with the square root of the total measurement time assuming the shot noise limit, which should be valid as long as the measurement time does not exceed about 10 seconds.

The capability of the arrangement to reject stray light is mainly a function of the spectral profiles of the Raman scatter line and the absorption line of the metal in the RID. To obtain the highest spectral resolution and lowest Raman shift, a narrow band tunable laser of much less than $0.01$ cm$^{-1}$, such as a single mode diode laser or a ring dye laser, a glow discharge RID, or a photoionization RID (rather than collisional ionization) must be used. Photoionization from the excited level of the metal in the RID will require an intense dye laser (much greater than $10^{25}$ photons/centimeters$^2$).

The present arrangement should be ideally suited to the detection of Raman scatter in highly scattering media, such as silver substrate, silver electrodes, and silver sols used in surface enhanced Raman and to the detection of resonance Raman scatter in the presence of a fluorescence background. In the case of scatter or fluorescence, only radiation within several half-width of the absorption line of metal in the RID will result in an appreciable signal and thus in appreciable noise. In the case of fluorescence, the detected fluorescence signal can be quite small (say $10^{-3}$ to $10^{-4}$ of the Raman signal) and the efficiency with which the Raman signal is detected will be unity only if the peak fluorescence also occurs at the first wavelength. In the case of scatter, the interferent signal will be small since the scatter appears at a wavelength other than the first wavelength. Accordingly, the only contribution is a result of overlap of the scattered spectral profile and the absorption spectral profile of the metal in the RID. Finally the contribution of RFI can be made small by appropriate laser shielding.

This RID approach to Raman should allow the measurement of analytes in high scattering environments such as those occurring in work with catalysts and other solid materials as well as in Surface Enhanced Raman Spectrometry, SERS. Because of the high spectral resolution and the use of metals with the first transition wavelength much greater than 7000 Å, fluorescence should not be a problem. Finally, except for the pulsed (or cw) dye laser system, the system is simple requiring few optics, no spectrometer or interferometer, and no photodetectors which have detection efficiencies less than unity. The RID approach is not only unique but also contains measurements not previously possible either due to detection efficiency, resolution, or scatter problems.

Although various specific constructions and materials have been described herein, it is to be understood that these are for illustrative purposes only. Various modifications and adaptations will be apparent to those of skill in the art. Accordingly, the scope of the present invention should be determined by reference to the claims appended hereto.

What is claimed is:

1. An apparatus for Raman spectroscopy comprising:
   a sample cell for holding sample material upon which Raman analysis is to be performed;
   a first laser source, which is tunable for applying laser energy having a variable wave number to sample material within the sample cell;
   a resonance ionization detector having a metal vapor which exists at lower, intermediate, and higher energy levels, said higher energy level being at or near ionization, a difference between said lower and intermediate energy levels corresponding to a first transition energy, a difference between said intermediate higher energy levels corresponding to a second transition energy;
   a second laser source for applying energy having a known wave number to said metal vapor of said ionization detector, said known wave number corresponding to one of said first and second transition energies; and
   an optical coupler to supply Raman scatter from said sample cell to said resonance ionization detector such that, upon the first laser source being tuned to produce Raman scatter at a wave number corresponding to the other of said first and second transition energies, ionization is detected by said resonance ionization detector.

2. The apparatus of claim 1 wherein said resonance ionization detector is selected from the group consisting of a flame ionization detector, and a glow discharge tube ionization detector.

3. The apparatus of claim 1 wherein said resonance ionization detector is a flame ionization detector.

4. The apparatus of claim 1 wherein said resonance ionization detector is a glow discharge tube ionization detector.

5. The apparatus of claim 1 wherein said metal vapor is a metal selected from the group consisting of the Group I A, II B, III A, or IV A.

6. The apparatus of claim 6 wherein said metal vapor is selected from the group consisting of lithium and lead.

7. The apparatus of claim 1 wherein said known wave number corresponds to said second transition energy and the first transition energy is provided by the Raman scatter.

8. The apparatus of claim 1 further comprising a spectra recorder operably connected to said resonance ionization detector for recording a Raman spectra of the sample material.

9. A method of Raman spectroscopy comprising the steps of:

placing sample material for Raman analysis in a sample cell;

applying laser energy of a variable wave number to said sample material within the sample cell;

generating a metal vapor within a resonance ionization detector, the metal vapor existing at lower, intermediate, and higher energy levels, said higher energy level being at or near ionization, a difference between said lower and intermediate energy levels corresponding to a first transition energy, a difference between said intermediate and higher energy levels corresponding to a second transition energy;

applying laser energy to said metal vapor at a known wave number corresponding to one of said first and second transition energies; and coupling Raman scatter from said sample cell to said resonance ionization detector such that, upon the laser energy of variable wave number being tuned to produce Raman scatter at a wave number corresponding to the other of said first and second transition energies, ionization is detected by said resonance ionization detector.

10. The method of claim 9 wherein said known wave number corresponds to said second transition energy and the first transition energy is provided by the Raman scatter.

11. The method of claim 10 wherein said resonance ionization detector is selected from the group consisting of a flame ionization detector, and a glow discharge tube ionization detector.

12. The method of claim 10 wherein said metal vapor is a metal selected from the group consisting of the Group I A, II B, III A, or IV A.

13. The method of claim 12 wherein said metal vapor is selected from the group consisting of lithium and lead.

14. The method of claim 9 further comprising the step of recording a Raman spectra of the sample material.

15. The method of claim 14 wherein said metal vapor is a metal selected from the group consisting of the Group I A, II B, III A, or IV A.

16. The method of claim 15 wherein said resonance ionization detector is a flame ionization detector.

17. The method of claim 15 wherein said resonance ionization detector is a glow discharge tube ionization detector.

* * * * *

UNITED STATES PATENT AND TRADEMARK OFFICE
CERTIFICATE OF CORRECTION

PATENT NO. :     5,088,820

DATED      :     February 18, 1992

INVENTOR(S) :    James D. WINEFORDNER, ET AL

It is certified that error appears in the above-identified patent and that said Letters Patent is hereby corrected as shown below:

On the title page, item 57, line 17 of the Abstract: delete "for" and insert -- or --.

In column 8, line 13 of claim 1: after "intermediate" insert -- and --.

In column 9, line 1 of claim 9: delete "of" and insert -- for --.

Signed and Sealed this

Thirteenth Day of April, 1993

*Attest:*

STEPHEN G. KUNIN

*Attesting Officer*     *Acting Commissioner of Patents and Trademarks*